United States Patent [19]

Yamauchi et al.

[11] 4,203,100
[45] May 13, 1980

[54] LIGHT DECREASE TYPE SMOKE SENSOR

[75] Inventors: Yukio Yamauchi, Kawasaki; Hiroshi Homma, Tokyo, both of Japan

[73] Assignee: Hochiki Corporation, Tokyo, Japan

[21] Appl. No.: 907,466

[22] Filed: May 19, 1978

[30] Foreign Application Priority Data

May 23, 1977 [JP] Japan ................. 52-58864

[51] Int. Cl.² ............................................. G08B 17/10
[52] U.S. Cl. ..................................... 340/630; 250/573
[58] Field of Search ............... 340/628, 630; 250/573

[56] References Cited

U.S. PATENT DOCUMENTS

| | | | |
|---|---|---|---|
| 3,846,772 | 11/1974 | Peberdy | 340/630 |
| 3,919,702 | 11/1975 | Hayes et al. | 340/630 |
| 4,011,458 | 3/1977 | Malinowski | 340/630 X |

*Primary Examiner*—John W. Caldwell, Sr.
*Assistant Examiner*—Daniel Myer
*Attorney, Agent, or Firm*—Frank J. Jordan

[57] ABSTRACT

A smoke detector includes a light-emitting circuit, a light-receiving circuit, a smoke detecting space between the light-emitting and receiving circuits, and an amplifier circuit connected to the light-receiving circuit amplifying the output of the light-receiving circuit at an output terminal. An output comparison circuit is provided having an input terminal connected to the output terminal of the amplifier circuit and a voltage memory circuit is connected to another input terminal of the output comparison circuit. A detector circuit has one input terminal connected to the memory circuit and another input terminal connected to the output terminal of the comparison circuit, and a fire alarm circuit is connected to the detector circuit for operating an alarm when smoke from a fire fills such space between the light-emitting and receiving circuits, whereby contamination due to time and environmental factors has a minimal adverse effect on the detection of smoke in such space.

12 Claims, 7 Drawing Figures

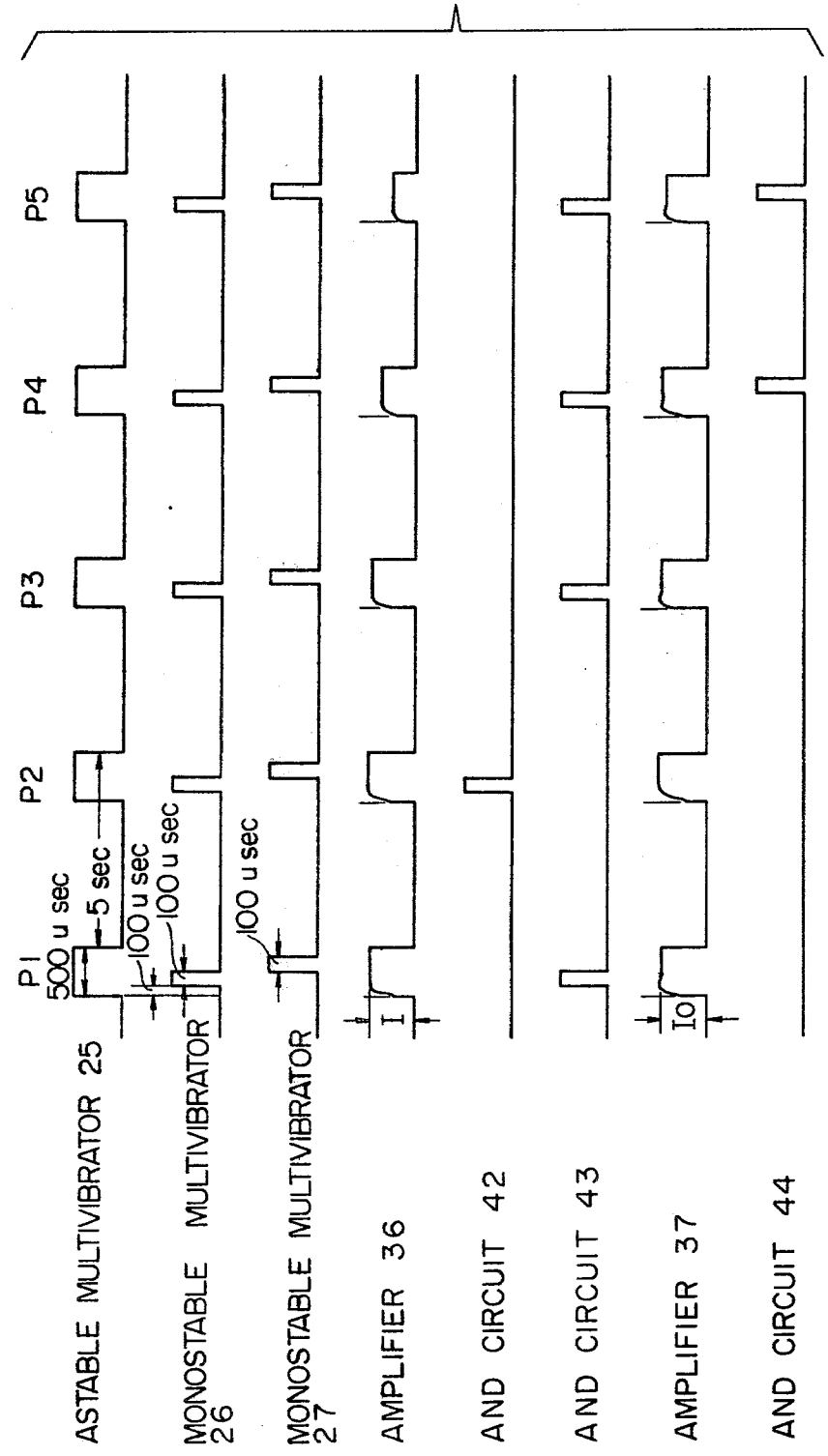

ical embodiment of the invention, and

LIGHT DECREASE TYPE SMOKE SENSOR

BACKGROUND OF THE INVENTION

1. Field of the Invention

The present invention relates to a light-depreciation type smoke detector and, more particularly, to a smoke detector which is not sensitive to the depreciation of light attributable to secular change, or a change of ambient temperature, but can produce an alarm upon detection of an average smoldering fire, within an acceptable time.

2. Description of the Prior Art

A known typical conventional light-depreciation type smoke detector is disclosed in U.S. Pat. No. 3,846,772.

Such detector incorporates a comparator adapted to produce an output when the voltage differential between a first and a second electric signals, which vary depending on the amount of received light and are input to the comparator at a suitable interval, comes to exceed a predetermined threshold voltage. In order that the second input signal may suitably be compared with the first input signal, a capacitor for holding the voltage of the first input signal, and another capacitor for holding the voltage of the second input signals are connected to respective terminals of the comparator.

The output from the comparator is obtainable only when a reduction in the amount of the received light corresponding to the above mentioned threshold voltage for the functioning of the comparator takes place in the period from the time of receipt of the first input signal to the time of receipt of the second input signal. However, in case of a smoldering fire in which the reduction of the amount of light takes place in quite a slow and gentle manner, a change of the voltage of the first input signal tends to occur, making it difficult to correctly make use of the predetermined voltage differential between the first and the second inputs.

SUMMARY OF THE INVENTION

It is therefore an object of the present invention to provide a highly reliable light-depreciation type smoke detector, having a comparator to one input terminal of which is delivered a pulse signal corresponding to the amount of light received by a light receiving element, while a voltage memorized by a suitable memory device, or memoriode, connected to the other input terminal is synchronously corrected by a correcting constant-value pulse produced in accordance with the amplitude of the pulse signal from the light receiving element, so that the change of condition of the smoke detector due to a secular change or contamination by the dusts during a long use is suitably negated by the aforementioned correction of the memorized voltage by the correcting constant-value pulse signal.

It is another object of the invention to provide a light-depreciation type smoke detector, in which the value of the correcting constant-value pulse can be changed in accordance with the contaminating condition in the place at which the detector is to be installed, expectable temperature change, secular change and other conditions, so as to afford an optimum operating condition of the detector.

It is still another object of the invention to provide a light-depreciation type smoke detector in which, in order to detect a smoldering fire in which the reduction rate of the light input is small, the aforementioned correcting constant-value pulse is made to have a value which is smaller than the change of the light input per unit time, obtained through dividing the differential between the light inputs at the starting and the finishing times of the detecting period of the time length of the detecting period.

BRIEF DESCRIPTION OF THE DRAWINGS

FIG. 7 is a graph of time/amplitude output wave forms of various multivibrators, amplifiers and AND circuits thereof.

DETAILED DESCRIPTION OF THE PREFERRED EMBODIMENTS

According to the result of a smoldering fire-smoke test, the rate at which light transmission is decreased by the smoke of an average smoldering fire becomes substantially constant about one hour after the beginning of the fire, and assumes a value of about 40%/hour per 30 cm.

On the other hand, the rate at which the amount of received light is decreased due to the secular change caused by the contamination of light emitting element, light receiving element and the path of light by dusts and vapor of oil, as well as by the deterioration of the performance of the circuit elements, during a long use of the detector, is considered to be less than 10%/day.

At the same time, the rate at which the amount of the received light is decreased by a change of the ambient temperature, which takes place in such a season as one having a large temperature variation, or soon after the start of an air conditioner in winter and summer seasons, can be limited to less than 10%/hour.

A light-depreciation type smoke detector capable of producing an alarm signal after a practical time of about 3 hours from the time of commencement of an average smoldering fire, but not sensitive to secular change and ambient temperature change, is obtained when the distance between the light emitting and receiving sections, rate of correction of the memorized voltage and the ratio of the voltage across the memoriode to the voltage corresponding to the light input by which the alarm circuit is actuated, respectively, are 30 cm, 12%/hour and 1:2.

A preferred embodiment of the invention will be described with reference to FIG. 1.

Figure 1:
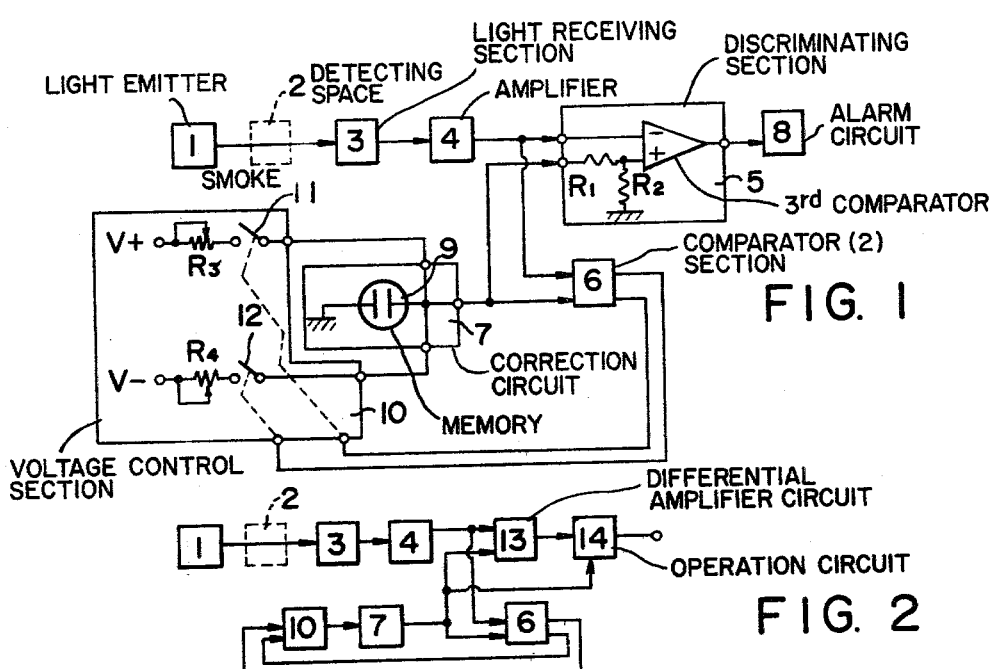
FIG. 1 is a block diagram showing one embodiment of the invention.

Referring to FIG. 1, the reference numeral 1 denotes a light-emitting section consisting of a light-emitting element, lenses and so forth. The light emitted from the light emitting section is delivered to a light-receiving section 3 consisting of a light-receiving element and lenses, through a detecting space 2. Such light is depreciated by the presence of smoke in the detecting space 2, and the light-receiving section 3 produces an electric output corresponding to the amount of the light actually received by section 3.

This electric output from section 3 is amplified by an amplifier 4, and the amplified electric output is delivered to a discriminating section 5 including a detection circuit, and to a comparator circuit 6.

The discriminating section 5 and the comparator circuit 6 perform a comparison of the amplified electric output with the output from a correction, or memory section 7. An alarm circuit 8 is actuated to drive an alarm, such as a bell, when a predetermined ratio of the electric signal from the amplifier 4 to the output from the memory section 7 is reached.

The discriminating section 5 includes a third comparator having an OP amplifier, and resistors $R_1, R_2$ adjustable to give any desired light-depreciation by which the alarm circuit 8 is to be driven. More specifically, the output of the third comparator is inverted to activate the alarm circuit 8, when the output from the amplifier 4 drops below 90% of the output from the memory section 7, i.e. when the light-depreciation has grown larger than 10%, provided that the ratio of the resistances $R_1:R_2$ has been selected to be 1:9.

The memory section 7 comprises a voltage memoriode or memory element 9 which may be an electrolytic voltage memory in which the voltage difference between two electrodes in an electrolyte is changed in dependency on the integration of the current between these electrodes, by the ion movement through the electrolyte.

A voltage control section 10 has a switch 11 adapted to deliver a positive voltage V+ to the memory element 9 through a resistance $R_3$, and a switch 12 adapted to deliver a negative voltage V− to the memory element 9 through a resistance R4. These switches 11,12 constitute a switching circuit which is adapted to be opened and closed in accordance with the output from the comparator circuit 6.

More specifically, the switch 11 is closed, for instance, when the output from the memory section 7 is small as compared with the output from the amplifier 4, so as to complete a circuit for charging the memory element 9 from the positive voltage source V+. Consequently, the output from the memory section 7 approaches the level of the output from the amplifier 4, at a long time constant. On the contrary, when the output from the memory section 7 is large as compared with the output from the amplifier 4, the switch 12 is closed to complete a circuit for discharging from the memory element 9 to the negative voltage source V−, so that the output from the memory section 7 is gradually lowered and approaches the output from the amplifier 4 with a long time constant.

The switches 11, 12 are opened when the output from the amplifier 4 and that from the memory section 7 are equal. Consequently, the charging and discharging to and from the memory element 9 are not performed, and the level of the output from the memory section 7 is maintained.

Since the charging and discharging of the memory element 9 are effected gradually through the resistances $R_3$ and $R_4$, the output from the memory section 7 can follow the change of the output from the amplifier 4 attributable to the contamination of lenses, secular change of the light emitting and receiving elements, and a temperature change over a long period. Consequently, the discriminating section 5, which discriminates the output from the amplifier 4 from the output from the memory section 7, cannot detect the lowering of the level of the output from the amplifier 4 attributable to the contamination of the lenses and the like reasons.

However, when the rate at which the level of output from the amplifier 4 is lowered has become large, due to the presence of the smoke or the like, the output from the memory section 7 cannot follow this change, so that the lowering of the level of the output from the amplifier 4 with respect to the output from the memory section 7 is detected by the discriminating section 5, so as to cause actuation of the alarm circuit 8.

In case that a large "noise" light, such as the flash light of a camera, is received by the light-receiving section 3, the memory element 9 is charged if the level of this "noise" light is large enough to make the level of the output from the amplifier 4 larger than the level of the output from the memory section 7. However, the charging current is controlled by the resistance $R_3$ and, therefore, cannot cause a substantial change of the output from the memory section 7, in the short time which the "noise" light lasts. Consequently, there is no chance of any error sufficient to cause a false alarm.

Figure 2:
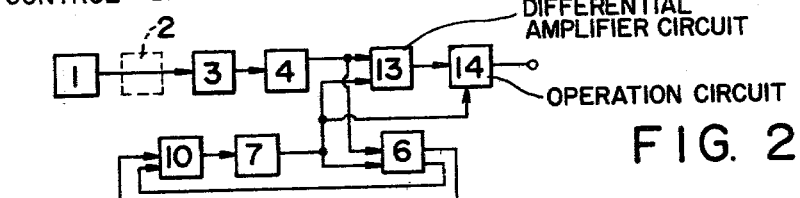
FIGS. 2 to 5 are block diagrams of different modifications of the invention.

FIG. 2 shows an embodiment in which the present invention is applied to an analog sensor. In FIG. 2, the same reference numerals to those of FIG. 1 denote the same or equivalent parts.

Reference numeral 13 denotes a differential amplifier circuit. Representing the outputs from the amplifier 4 and the memory section 7, respectively, by I and Io, the differential amplifier circuits produces an output which is in proportion to the differential I−Io, i.e. to the depreciation of the light.

An operation circuit 14 is adapted to produce a signal corresponding to the light-depreciation ratio which is obtained through dividing the output K(I−Io) (K is a constant) from the differential amplifier 13 by the output Io from the memory section 7, i.e. an output represented by K(I−Io/Io).

Figure 3:
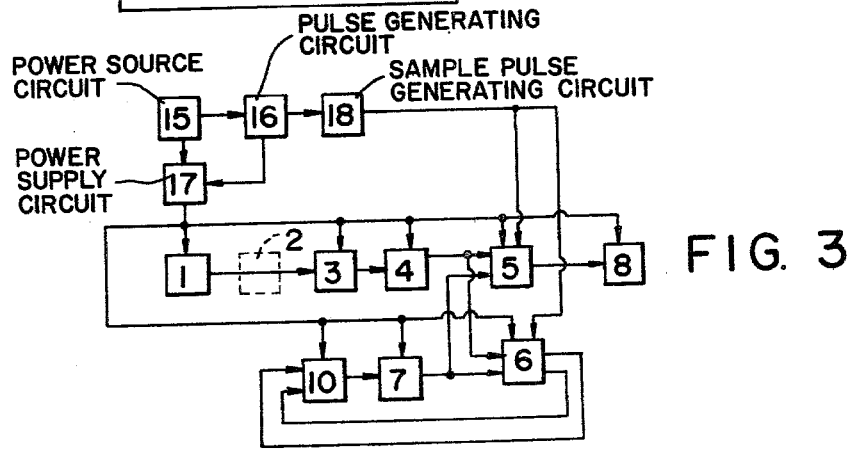

FIG. 3 shows an embodiment in which the detector in accordance with the invention is driven by pulses, in order to reduce the power consumption. The voltage memory element is suitable for operation by pulses, since its content is never changed even when the power supply is interrupted.

In FIG. 3, reference numerals 1–8 denote the same or equivalent parts as those of FIG. 1. A power source circuit 15 energizes a pulse generating or oscillation circuit 16 adapted to produce a pulse train of a constant duty ratio of, for example, 5 seconds period and 1 m sec pulse width. Such pulse train is delivered to various parts of the detector through a power supply circuit 17.

A sampling pulse generating or oscillation circuit 18 is adapted to deliver sampling pulses of 0.1 m sec width to the comparator circuit 6 and the discriminating section 5, after an elapse of a time of, for example, 0.5 m sec, from the time of supply of the power pulse to the circuits of the device until the operations of these circuits are stabilized, so as to avoid erroneous operations due to the unstable operations of these circuits which are likely to take place immediately after the application of the power pulses.

The use of pulses as described above is effective not only in diminishing the power consumption but also in affording an easy adjustment of the time constant for the charging and discharging of the voltage memory device. Namely, the time constant of the memory circuit constituted by voltage memory element is determined, in case of a pulse drive, by the duty ratio of the output pulse applied to the controlling section of the comparator circuit 6, and by the peak value of the charging and discharging current of the voltage memory device. For instance, provided that the time constant of the memory section 7 has been selected to be 10 hour/100% (the voltage memory element is charged from 0% up to 100% in 10 hours), 10 hours are required for obtaining the settled condition of the device for the first time after the first power supply to the device following the completion of the assembling of the device.

This time can be shortened by making the duty ratio of the pulse train from the pulse generating circuit 16 adjustable externally. For instance assuming that the duty ratio of the pulse train is 1 m sec/5 sec and that the time constant of the memory section 7 is 10 hours/100%, the time constant can be reduced to 1/100, i.e. to 6 minutes/100%, by externally increasing the duty ratio by 100 times, i.e. to 1 m sec/50 m sec.

At the same time, it is effective and recommended from a viewpoint of protective maintenance by making the time constant of the memory section 7 remotely from, for example, a central control station, after the installation of the detector.

Figure 4:
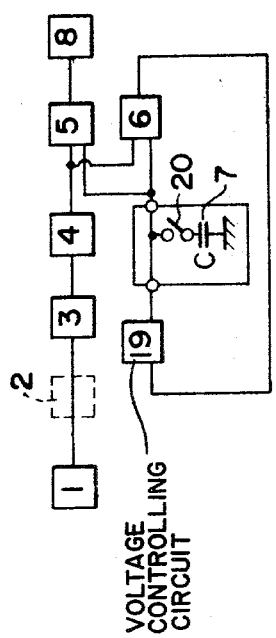

FIG. 4 shows another embodiment of the invention, in wihich a capacitor C is used in place of the voltage memory device or element. In FIG. 4, the reference numerals 1-8 denote the same or equivalent parts as those of FIG. 1. A voltage controlling section 19 is adapted to charge the capacitor C at the initial stage at which the capacitor C has not been charged, so as to make the output from the memory section 7 equal to the output from the amplifier 4.

The charging of the capacitor C by the voltage controlling section 19 is effected gradually with a long time constant. However, it is preferred to provide switching means so as to afford a quick charge of the capacitor C in the above mentioned initial stage.

The capacitor C has a leak current of a long time constant. A contact 20 is provided for checking the leak current flowing from the capacitor C to the voltage controlling section 19, or to the comparator circuit 6, and is adapted to be intermittently opened and closed by means of relays which are not shown.

In the detector of FIG. 4, the voltage across the capacitor C is gradually lowered by the aforementioned leak current, when the level of the output from the amplifier 4 is gradually lowered as is the case of the contamination of the lenses, so that the output from the amplifier 4 comes equal to the output from the memory section 7. At the same time, the voltage across the capacitor C is not changed substantially by a large noise light which lasts only for a short time, and can maintain the initial condition. In addition, when the output from the amplifier 4 is gradually changed by the temperature change over a day or seasons, the voltage across the capacitor C is also changed gradually to maintain the proper amount of content.

In case of a depreciation of light due to the presence of the smoke, the level of the output from the light-receiving section 3 is drastically lowered, but the output from the memory section 7 is not changed substantially, so that the alarm circuit 8 is actuated by the discriminating section 5.

Figure 5:
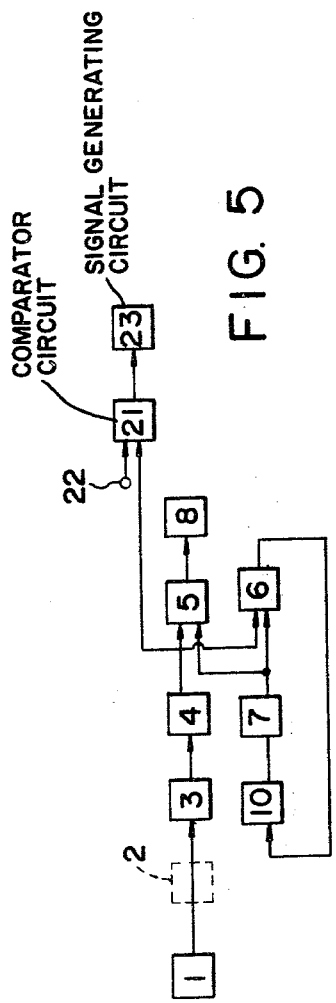

FIG. 5 shows still another embodiment adapted to produce a maintenance demand signal before making an erroneous operation, when the lenses are extraordinarily contaminated or when the light-emitting and/or light-receiving elements are extraordinarily deteriorated. In FIG. 5, the reference numerals 1-8 denote the same or equivalent parts as those of FIG. 1.

A comparator circuit 21 is adapted to compare the output from the amplifier 4 with a reference signal from a terminal 22, so that a maintenance demand signal generating circuit 23 may be driven when the output level of the amplifier 4 drops below a predetermined level.

Figure 6:
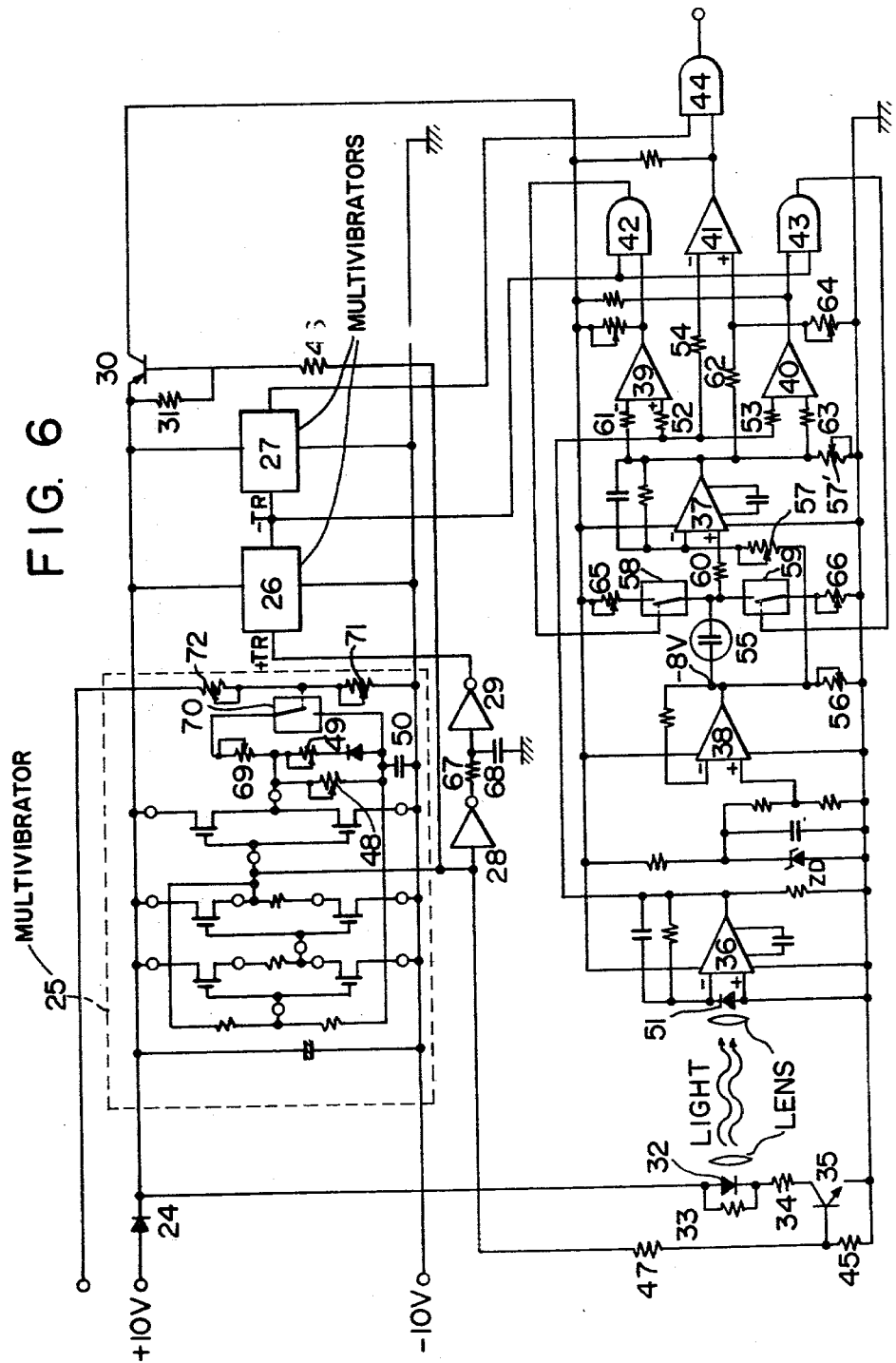
FIG. 6 is an electric circuit diagram of a practical embodiment of the invention.

A practical example of the circuit incorporated in an embodiment of the invention is described in detail hereinafter, with specific reference to FIG. 6.

A plus-side terminal of a ±10 V D.C. power source is connected to a diode 24. The diode 24 is connected at its other side to the pulse-side terminals of a stable, multivibrator, or non-stable multiple vibrator 25, to monostable multivibrators 26, 27, and to inverters 28,29. The diode 24 is also connected to the emitter of a transistor 30, to a resistance 31, to a light-emitting diode 32, and to a resistance 33. The other sides of the light-emitting diode 32 and the resistance 33 are connected to a resistance 34 which, in turn, is connected at its other side to the collector of a transistor 35. The collector of the transistor 35 is connected to the plus sides of amplifiers 36,37, to constant-voltage source 38, to comparators 39,40,41, and to AND circuit 42,43,44.

The minus side or ground terminal of the 10 V D.C. source is connected to the minus sides of the power input terminals of the non-stable multivibrator 26,27, to inverters 28,29, to amplifiers 36,37, to constant voltage source 38, to comparators 38,40,41, and to AND circuits 42,43,44, and is suitably grounded. The −10 V output terminal of the D.C. source is connected also to the emitter of the transistor 35 and to a resistance 45. The base of the transistor 30 and the other side of the resistance 31 are connected to a resistance 46 which, in turn, is connected at its other end to the output terminal of the non-stable multiple vibrator 25. The base of the transistor 35 is connected to the other side of the resistance 45 and to a resistance 47 which is connected at its other side to the output terminal of the non-stable multivibrator 25.

The ±10 V D.C. voltage is thus applied to the non-stable multiple vibrator 25, monostable multple vibrators 26,27 and inverters 28,29, as the source power. Meanwhile, the transistors 30,35 function as switches in accordance with the output from the non-stable multivibrator 25, so as to supply the light-emitting diode 32, amplifiers 36,37, constant voltage source 38, comparators 39,40,41, and AND circuits 42, 43,44, with pulse voltages of ±10 V. The pulse interval and the pulse width of the pulse voltage, i.e. the pulse interval and the pulse voltage of the non-stable multiple vibrator 25 are determined by resistances 48,49 and the capacitance of a capacitor 50.

The resistances 33,34 are provided for the purpose of temperature-compensation of the light-emitting diode 32. The resistances 31,46 are for regulating voltage for controlling the opening and closing of the switch constituted by the transistor 30, while the resistances 45,47 are provided for regulating the voltage by which the opening and closing of the switch constituted by the transistor 35 is controlled.

The diode 24 functions to prevent any reverse voltage acting on the circuit.

A photo diode 51 is connected at its terminals to the corresponding terminals of an amplifier 36, so that the output current of such photo diode may be amplified. Namely, the electric signal appearing at the output terminals of the photo diode, corresponding to the light emitted from the light-emitting diode 32, is amplified by the amplifier 36. The output terminal of the amplifier 36 is connected to resistances 52,53,54. The other sides of the resistances 52,53 and 54 are connected, respectively, to one input terminals of the comparator 39, comparator 40, and the comparator 41.

The output terminal of the constant voltage source 38 which gives a charging and discharging reference to a memoriode (voltage memory element) 55 is connected to the memoriode 55, so as to maintain the potential of one end of the memoriode 55 at a constant level of −8V. The output of the constant voltage source 38 is commonly connected also to resistances 56,57. The resistance 57 is connected at its other side to the minus-side input of the amplifier 37.

The other side of the memoriode 55 is connected to bilateral switches (switches which are opened and closed when the control terminals are maintained at high and low levels) 58,59 and to a resistance 60.

The other end of the resistance 60 is connected to the plus-side input terminal of the amplifier 37, while the other side of the resistance 56 is grounded. Thus, the voltage across the memoriode 55 is amplified by means of the amplifier 37. The resistances 57 and 57' are provided for adjusting the amplitude of the amplifier 37, and the resistance 60 controls the input level to the amplifier 37.

The output terminal of the amplifier 37 is connected to resistances 61,62,63. The other sides of the resistances 61,62 and 63 are connected, respectively, to the other input terminals of the comparators 39,40 and 41. The input terminal of the comparator 41 is also connected to a resistance 64 which is grounded at its other side.

Thus, the comparators 39,40 and 41 function to produce output signals in accordance with the ratio of the voltage obtained by amplifying the voltage across the photo diode 51 to the voltage obtained through amplifying the voltage across the memoriode 55.

The resistances 61,52,53,63,54 act as input protection, and the resistances 62 and 64 for adjusting the input level to the comparators, in other words for adjusting the points at which the outputs are produced in respective comparators.

The output terminals of the comparators 39,40 are connected to the input terminals of the AND circuits 42,43, while the other input terminals of the AND circuits 42,43 are connected to the output terminal of the monostable multivibrator 26. The output terminals of the AND circuits 42,43 are connected to the control terminals of the bilateral switches 58,59. The other side of the bilateral switch 58 is connected to a resistance 65 which in turn is connected at its other side to the collector of the transistor 30. The other bilateral switch 59 is connected to a resistance 66 which is grounded at its other side.

The AND circuit 42 thus controls the opening and closing of the bilateral switch 58 for charging the memoriode 55, in response to the output from the monostable multivibrator 26 and to the output from the comparator 39 which is adapted to produce an output in accordance with the ratio of the voltage obtained through amplifying the voltage across the photo diode 51 and the voltage obtained through amplifying the voltage across the memoriode 55.

The AND circuit 43 controls the opening and closing of the bilateral switch 59 for discharging from the memoriode 55, in response to the output from the monostable multivibrator 26 and the output from the comparator 40 which functions contrary to the comparator 39. The resistances 65 and 66 are provided, respectively, for adjusting the charging and discharging speeds.

The output terminal of the comparator 41 is connected to the input terminal of the AND circuit, while the other input terminal of the AND circuit 44 is connected to the output terminal of the monostable multivibrator 27. The AND circuit thus functions to actuate the alarm circuit, in response to the output from the monostable multivibrator 27 and to the output from the comparator 41 which produces the output in accordance with the ratio of the voltage obtained through amplifying the output current of the photo diode 51 to the voltage obtained through amplifying the voltage across the memoriode 55.

The output terminal of the non-stable multivibrator 25 is connected to the input terminal of inverter 28 which is connected at its output side to a resistance 67. The resistance 67 is connected at its other side to the input terminal of inverter 29 and to a capacitor 68 which, in turn, is grounded at its other side.

The plus-side trigger terminal of the monostable multivibrator 26 is connected to the output terminal of the inverter 29. At the same time, the minus-side trigger terminal of the monostable multivibrator 27 is connected to the output terminal of the multivibrator 26. The monostable multivibrator 26 thus can produce a pulse at a time lag determined by the resistance 67 and the capacitance of the capacitor 68 behind the starting end of the pulse produced by the non-stable multivibrator 25, while the monostable multivibrator 27 produces a pulse which starts at the time of the ending of the pulse generated by the monostable multivibrator 26.

A resistance 69 is connected to one end of the resistance 48 which is adapted to adjust the pulse interval of the pulses generated by the non-stable multivibrator 25. The resistance 69 is connected at its other end to a bilateral switch 70.

The bilateral switch 70 is connected at its other end to the other end of the resistance 48, while the controlling end of the same is connected to resistances 71,72. The resistance 71 is grounded at its other end. The value of the resistance 69 is selected sufficiently smaller than the resistance 48. The bilateral switch 70 is closed, as another D.C. current is supplied between the grounding and the other end of the resistance 72, so that pulses of a pulse width much smaller than the pulse determined by the resistance 48 and the capacitance of the capacitor 50 is generated by the non-stable multivibrator 25. Consequently, the memoriode 55 can be charged in a much shorter time.

The resistances 71,72 are provided for adjusting the voltage for controlling the opening and closing of the bilateral switch 70, while the resistance 69 is provided for adjusting the pulse interval. This operation is effected in case it is necessary to diminish the long dead time in which the device is is inoperative, from the time of the starting of the device to the completion of the charging of the memoriode 55.

In normal operation, the gains of the amplifiers 36,37 and other conditions are so selected that the voltage across the memoriode 55 becomes 40 mV. In such case, about 0.33 $\mu$A·hour of charge is loaded in the memoriode 55. This electric charge of 0.33 $\mu$A·hour will be consumed by an intermittent discharge by pulses of 2mA, a pulse interval of 5 sec, and pulse width of 100 $\mu$sec, within 500 minutes.

That is to say, the discharge voltage rate, i.e. the rate of correction of the memorized voltage is 100%/500 min., 12%/hour. For charging and discharging the memoriode 55 with a pulse current of 2 mA, the resistances 65 and the resistance 66 for setting the charging and discharging rates are adjusted to 9 KΩ and 1 KΩ, respectively, because one end of the memoriode 55 is maintained at the potential of −8V, so as to obtain the aforementioned rate of correction of the memorized voltage of 12%/hour.

FIG. 7 shows output wave forms of the various multiple vibrators, amplifiers and AND circuits incorporated in the described embodiment of the invention.

The output wave forms of the non-stable multivibrator 25, monostable multivibrator 26, monostable multivibrator 27, amplifier 36, AND circuit 42, AND circuit 43, amplifier 37 and the AND circuit 44, respectively, are shown in FIG. 7, as viewed from the upper side of FIG. 7.

Thus, the resistances 48,49 and the capacitance of the capacitor 50 are so selected as to make the non-stable multivibrator 25 produce pulses of 500 μsec at a period of 5 seconds. At the same time, the resistance 67, and the capacitance of the capacitor 68 are so selected that the monostable multivibrator 26 produces its pulses at a time lag of 100 μseconds behind the starting end of the pulses of the non-stable multivibrator 25. In addition, the pulse widths of the pulses produced by the monostable multivibrator 26,27 are selected to be 100 μseconds.

Provided that the memoriode 55 has been charged at the starting time to such a level that its output Io is equal to the output I from the amplifier 36, if the level of the output I is lowered slightly in the period of the first pulse P-1, for any reason such as a temperature change or contamination, the AND circuit 43 provides its output in synchronization with the output from the monostable multivibrator 26, so that the bilateral switch 59 is closed over that period. Consequently, a discharge from the memoriode 55 is effected thus performing the correction of the level of the output Io.

The second pulse P-2 shows a slight increase of the output I. In this case, the AND circuit 42 provides its output in synchronization with the output from the monostable multivibrator 26, so that the bilateral switch 58 is closed over that period. Consequently, the memoriode 55 is charged to correct the level of the output Io.

Pulses P-3 to P-5 illustrate the operation of the detector in case of an abrupt or extraordinary change of the level of the output I, due to the presence of smoke between the light-receiving and light-emitting sections. In this case, although the level of Io is corrected successively, the rate of the correction is too small, so that the level of Io cannot follow the drastic change of the level of the output I. Consequently, as the ratio of I to Io drops below the threshold value at which the comparator 41 produces its output (P-4), the AND circuit 44 issues a pulse signal for actuating the alarm circuit, in synchronization with the output from the monostable multivibrator 27.

What is claimed is:

1. A light-depreciation type smoke detector comprising:
    a light emitter;
    a light receiver;
    a smoke detecting space between said light emitter and receiver;
    an amplifier connected to said light receiver for amplifying the output of said receiver;
    a differential amplifier circuit connected to said amplifier;
    a comparator circuit connected to the output of said amplifier circuit;
    a memory circuit connected to said comparator circuit and to said differential amplifier circuit, said memory circuit producing an output controlling the output of said differential amplifier which latter output is proportional to any depreciation of the light received by said receiver from said emitter through such smoke detecting space; and
    an alarm operating circuit connected to receive the output from said differential amplifier and the output from said memory circuit for producing a signal corresponding to the light depreciation ratio by dividing the output from said differential amplifier by the output from said memory circuit;
    whereby contamination due to age and environment of said light emitter and receiver are minimized.

2. A light-depreciation type smoke detector comprising:
    an oscillation circuit for generating pulses;
    a light generating circuit including a light-emitting element responsive to pulses from said oscillation circuit;
    a light responsive circuit including a light-receiving element adapted to produce pulses upon receipt of the light emitted from said light-emitting element;
    said light-emitting and light-receiving elements being shielded from ambient light so that the amount of the light received by said light-receiving element may be reduced correctly in response to smoke coming into the space between said light-emitting and light-receiving elements;
    a correction circuit including a memoriode connected at one end to said light responsive circuit, and two comparators having a high voltage terminal and a low voltage terminal connected to the other end of said memoriode, other input terminals of said comparators being connected to said light responsive circuit to receive said pulse signals, the output terminals of said comparators being connected to said other terminal of said memoriode so that the memorized voltage in said memoriode is increased or decreased by the outputs from said comparators;
    a detecting circuit comprising means to set a threshold therein, including a third comparator having a high-voltage terminal connected to said other terminal of said memoriode, said third comparator having a low-voltage terminal connected to said light responsive circuit so as to receive pulse signals therefrom;
    whereby said third comparator is turned on to produce an alarm when the level of said pulse signal is lowered at a rate larger than the rate at which said memorized voltage of said memoriode is lowered to make the difference between the levels of said pulse signal and said memorized voltage larger than a threshold set in said third comparator.

3. A light-depreciation type smoke detector as defined by claim 2, in which
    said memoriode in said correction circuit comprises:
    an electrolytic voltage memory in which the voltage difference between two electrodes in an electrolyte changes according to the integration of the current between said electrodes by ion movement through such electrolyte.

4. A light-depreciation type smoke detector as defined by claim 3, in which
a voltage control circuit is also provided which comprises:
a first switch adapted to deliver a positive voltage V+ to said memory through a first resistor; and
a second switch adapted to deliver a negative voltage V− to said memory through a second resistor;
a switching circuit including said switches adapted to be opened and closed in accordance with the output of said two comparators;
thereby charging and discharging the memory gradually through said resistors so that the output of said memory follows a change caused by contamination of the smoke detection light-emitting and receiving elements and said detection circuit which discriminates the output of said memory from the input thereof cannot detect a lowering of such input due to such contamination.

5. A light-depreciation type smoke detector as defined in claim 4, in which
an amplifier circuit is provided for amplifying the pulse output of said light responsive circuit before such pulse output is conducted to said third comparator, and to said correction circuit.

6. A smoke detector comprising:
a light-emitting circuit;
a light-receiving circuit;
a smoke detecting space between said light-emitting and receiving circuits;
an amplifier circuit connected to said light receiving circuit amplifying the output of said light-receiving circuit at an output terminal;
an output comparison circuit having an input terminal connected to the output terminal of said amplifier circuit;
a voltage memory circuit connected to another input terminal of said output comparison circuit;
a detector circuit having one input terminal connected to said memory circuit and another input terminal connected to the output terminal of said comparison circuit; and
a fire alarm circuit connected to said detector circuit for operating an alarm when smoke from a fire fills such space between the light-emitting and receiving circuits;
whereby contamination due to time and environmental factors has a minimal adverse effect on the detection of smoke in such space.

7. A smoke detector as defined by claim 6, in which a voltage control circuit is provided for periodically charging said memory circuit with a DC voltage of constant value through resistances and switches in series with such resistances.

8. A smoke detector as defined by claim 6, in which said detector circuit comprises an analog sensor.

9. A smoke detector as defined by claim 8, in which said analog sensor comprises a differential amplifier circuit for producing a differential proportional to the depreciation of light received by said light receiver circuit, and
an operation circuit for producing a signal in response to a set value of such light-depreciation ratio.

10. A smoke detector as defined by claim 6, in which are provided:
a power source circuit;
a main pulse generating circuit energized by said power source circuit for producing a pulse train of constant duty ratio;
a sampling pulse generating circuit connected to said main pulse generating circuit for delivering sampling pulses to said output comparison circuit until the operation of such circuit is stabilizing; and
a power supply circuit connected to said main and sampling pulse generating circuits for delivering a pulse train to various circuits of the detector.

11. A smoke detector as defined by claim 6, in which said voltage memory circuit comprises a capacitor; and
a voltage controlling circuit is provided to initially charge said capacitor with a relatively long time constant;
switch circuit means in said memory circuit to provide a quick charge of said capacitor in such initial stage, comprising an intermittently opened and closed contact for checking link current flowing from said capacitor to said voltage controlling circuit, and to said output comparing section;
whereby in the case of depreciation of light, the level of the output from said light receiving circuit is drastically lowered, but the output from said memory circuit is not changed substantially, so that the fire alarm circuit is actuated by said detector circuit.

12. A smoke detector as defined by claim 6, in which means are provided for comparing the output of said amplifier circuit with a reference signal; and
a maintenance demand signal generating circuit is connected to said means for producing such signal when the output level of said amplifier circuits drops below a predetermined level.

* * * * *